United States Patent
Van Gansberghe et al.

(10) Patent No.: US 11,306,332 B2
(45) Date of Patent: Apr. 19, 2022

(54) METHOD FOR SIMULTANEOUSLY PRODUCING LACTIC ACID AND ALCOHOL OR BIOGAS FROM CEREALS

(71) Applicant: FUTERRO S.A., Escanaffles (BE)

(72) Inventors: Frédéric Van Gansberghe, Escanaffles (BE); Philippe Coszach, Escanaffles (BE)

(73) Assignee: Futerro S.A., Escanaffles (BE)

( * ) Notice: Subject to any disclaimer, the term of this patent is extended or adjusted under 35 U.S.C. 154(b) by 380 days.

(21) Appl. No.: 16/605,168

(22) PCT Filed: Apr. 18, 2018

(86) PCT No.: PCT/EP2018/059861
§ 371 (c)(1),
(2) Date: Oct. 14, 2019

(87) PCT Pub. No.: WO2018/192952
PCT Pub. Date: Oct. 25, 2018

(65) Prior Publication Data
US 2020/0325504 A1 Oct. 15, 2020

(30) Foreign Application Priority Data
Apr. 20, 2017 (BE) .................. 2017/5275

(51) Int. Cl.
| | |
|---|---|
| *C12P 7/56* | (2006.01) |
| *C12M 1/107* | (2006.01) |
| *C12M 1/06* | (2006.01) |
| *C12M 1/00* | (2006.01) |
| *C12P 7/06* | (2006.01) |

(52) U.S. Cl.
CPC ............... *C12P 7/56* (2013.01); *C12M 21/04* (2013.01); *C12M 27/02* (2013.01); *C12M 29/00* (2013.01); *C12M 43/02* (2013.01); *C12P 7/06* (2013.01)

(58) Field of Classification Search
CPC .... C12P 7/56; C12P 5/023; C12P 7/06; C12P 7/16
See application file for complete search history.

(56) References Cited

U.S. PATENT DOCUMENTS
2,588,460 A    3/1952 Aries et al.

FOREIGN PATENT DOCUMENTS
| CA | 3036659 A1 * | 9/2019 | ............... C13K 1/06 |
|---|---|---|---|
| WO | 2013/148207 A2 | 10/2013 | |

OTHER PUBLICATIONS

John R P et al: "Direct lactic acid fermentation: Focus on simultaneous saccharification and lactic acid production", Biotechnology Advances, Elsevier Publishing, Barking, GB, vol. 27, No. 2, Mar. 1, 2009, pp. 145-152.
Gygene L et al.: "Efficiency of biogas production from corn bioe-thanol by-products using different inocula", 2013 4th International Youth Conference on Energy (ICYE), IEEE, Jun. 6, 2013, pp. 1-6.
Aug. 17, 2018, International Search Report and Written Opinion, European Patent Office, in PCT/EP2018/059861, which is the International application to this application.

* cited by examiner

*Primary Examiner* — Thane Underdahl
(74) *Attorney, Agent, or Firm* — Kolitch Romano LLP

(57) ABSTRACT

A process for the continuous production of lactic acid (a first fermentation product) and of a second fermentation product selected from the group consisting of alcohols and biogas, may include starting from the milling, necessarily carried out under dry conditions, of cereals and more particularly of corn. In the context of this process, a main flow and a flow of wastes which are difficult to ferment are recovered from the milling. These two flows are treated separately but simultaneously so as to produce, by fermentation, on the one hand, lactic acid and, on the other hand, an alcohol and/or biogas.

8 Claims, 1 Drawing Sheet

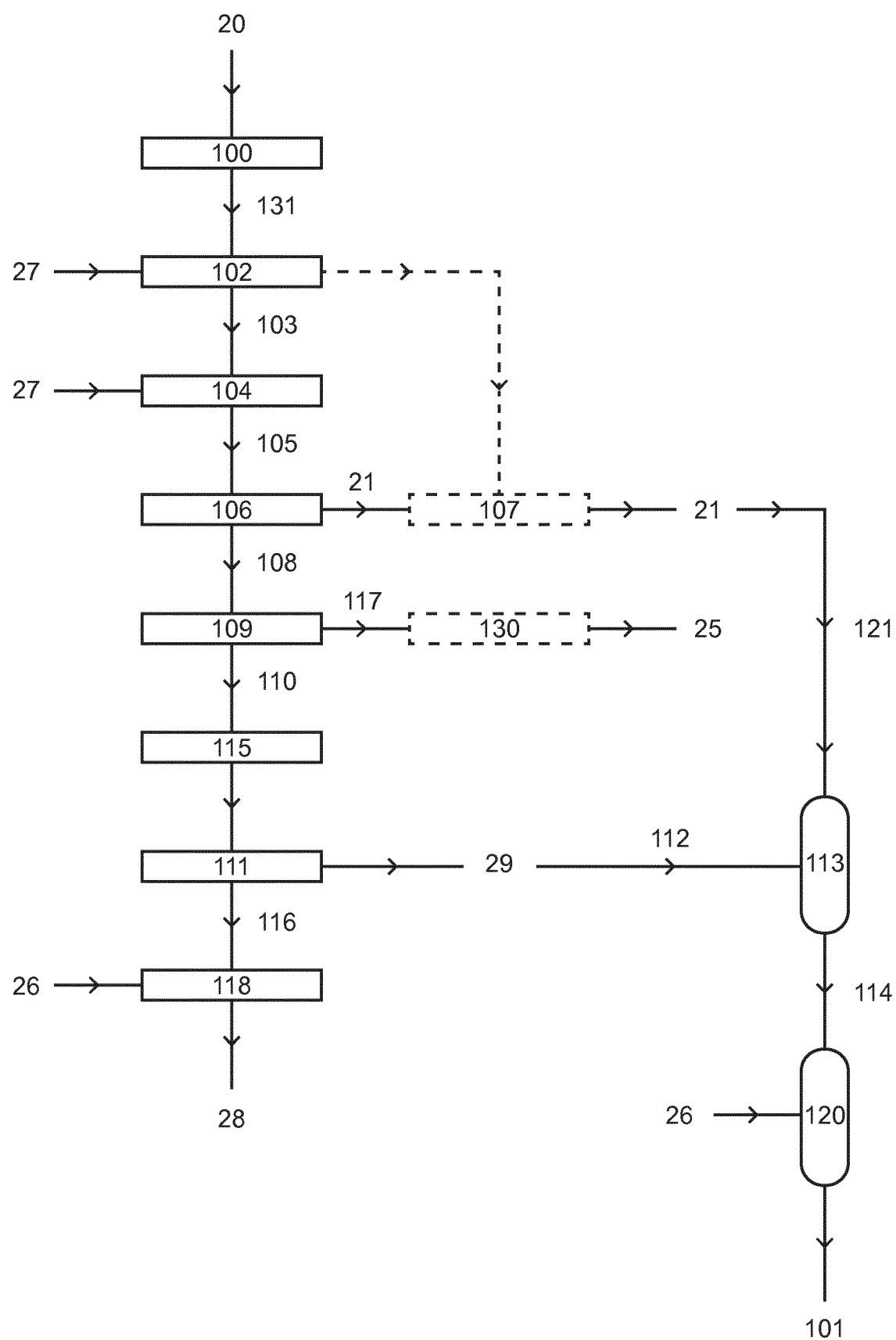

METHOD FOR SIMULTANEOUSLY PRODUCING LACTIC ACID AND ALCOHOL OR BIOGAS FROM CEREALS

INTRODUCTION

Subsequent to the liberalization of the sugar market, but also barriers to entry introduced at the European level, a marked bullish trend is becoming apparent with regard to the prices of the starting materials used in processes for the production from biochemical compounds of commodities such as biofuels (for example, bioethanol), citric acid, succinic acid, lactic acid, and the like. Consequently, it is becoming imperative for these industrial players to optimize their means of supply so as to have a starting material available in a large amount, at a competitive cost, and with a sufficient quality to make possible the viability of the biotechnology process without, however, requiring major adaptations of the pre-existing production units. In this context, several starting materials, such as, for example, corn, wheat, barley, sorghum, rice, rye, or oats, can be envisaged and more particularly corn may respond favorably to several of these criteria.

In the state of the art which relates to these processes for the treatment of cereals, it is known that the latter, corn cobs included in this, can be treated by wet milling or by dry milling and that dry milling is generally the simpler and the cheaper of the two operating routes.

It is also common practice to separate, on conclusion of the milling or later in the course of the process, the wastes comprising the fibers, the germs, and other products which are difficult to ferment, from the initial stream, which includes directly fermentable products.

This is furthermore described in the patent EP 3 121 258, which mentions the need to separate the undesirable components and also the components which are difficult to ferment before the fermentation for the production of biofuel, but also recommends not bothering about the separated fraction as its treatment requires sizeable capital costs which do not make possible a satisfactory economic upgrading of the process.

Currently, there exists no simple and relatively inexpensive process for producing both lactic acid (as a first fermentation product) and a second fermentation product, such as an alcohol and/or biogas, starting from cereal grains.

In point of fact, lactic acid is a product which finds new applications every day, in particular as a food preservative, but also in the synthesis of solvents or in biodegradable polymers. Moreover, after upgrading in the form of ethanol, the residual fraction of the secondary flow can also be upgraded in the preparation of livestock feed or in the form of other applications, such as, for example, biogas.

It is thus apparent that there exists a real need for a simple and relatively inexpensive process for producing both lactic acid and a second fermentation product starting from cereals, and more particularly starting from corn kernels or cobs.

SUMMARY

The present disclosure relates to a continuous process for the simultaneous production of lactic acid (as first fermentation product) and of a second fermentation product starting from cereals and in particular from corn kernels.

The process of the present disclosure comprises several stages, the main ones of which are the dry milling of the corn cobs, which will constitute the main flow, the separation, from this milling, of the wastes and other products which are difficult to ferment, which will constitute the secondary flow and which will be treated so as to produce alcohol and/or biogas, while the initial milled product (purified from the wastes and other products which are difficult to ferment) is treated separately so as to be subsequently fermented in a fermenter to produce lactic acid.

Another object of the process of the disclosure is to maximize the economic upgrading of corn kernels.

An object of the process of the present disclosure is to make possible the simultaneous production of lactic acid, as first fermentation product, and of a second fermentation product, starting from cereals, such as corn.

An object of the process of the present disclosure is to make possible the simultaneous production of lactic acid and of an alcohol, such as ethanol or butanol, starting from cereals, such as corn kernels or cobs.

An object of the process of the present disclosure is to make possible the simultaneous production of lactic acid and of biogas starting from cereals, such as corn kernels or cobs.

Another object of the process of the disclosure is to upgrade the part comprising the undesirable components and/or components which are difficult to ferment so as to convert them into alcohol or into biogas.

Another object of the disclosure is to maximize the economic upgrading of the treatment of cereals, in particular of corn kernels or cobs.

The applicant company has now found that it is possible to meet the aims described above by carrying out a process which comprises the following stages:

dry milling the corn kernels and/or cobs 20 in a mill 100;

recovering the flow 131 resulting from the milling and mixing it, in a mixer 102, with a stream of water (that is to say, to carry out a liquefaction stage) so as to create a slurry 103;

subjecting the slurry 103 to a saccharification stage 104 in a reactor and producing a crude dextrose stream 105;

separating the crude dextrose stream 105 into two flows, the first flow comprising a liquid dextrose flow 108 and the second dextrose flow comprising a solid part 21 comprising two flows resulting from two successive separation stages (by successively using two separators 106 and 107), and finally forming the flow 21;

separating, in a separator 109, the oil resulting from the milling and occurring in the liquid dextrose flow 108 and, on the one hand, recovering this oil for subsequent treatment (such as an oil refining stage 130) and, on the other hand, recovering a purified dextrose flow 110;

wherein:

the purified dextrose flow 110 is subjected to a stage of selective separation of the sugars 111 to recover a purified dextrose flow 116, which flow is purer than the flow 110, before subjecting it to a fermentation 118, and to recover, on the other hand, a flow rich in oligosaccharides 29;

the purified dextrose flow 116 is subjected to a fermentation 118 in the presence of a microorganism 26 appropriate for producing lactic acid 28;

the solid dextrose flow 21, resulting from two successive separation stages (by successively using two separators 106 and 107), is recovered via a pipe 121 containing the products which are difficult to ferment, and also a flow rich in oligosaccharides 29, which results from the selective separation of the sugars 111, is recovered via a pipe 112, so as to hydrolyze them in a reactor 113 under hydrolysis conditions and to convert them into a fermentable dextrose flow 114;

the fermentable dextrose flow 114 is subjected to a fermentation in a fermenter 120 to produce a second fermentation product 101, preferably selected from the group consisting of ethanol, butanol, and/or biogas.

It is clearly understood that both corn, on the one hand, and wheat, barley, sorghum, rye, rice, oats, or other similar products, on the other hand, are included as cereals.

The process of the present disclosure comprises a dry milling, in an appropriate mill 100, of cereals 20, in the case in point corn kernels and/or cobs, so as to simultaneously produce two separate flows of sugar or dextrose.

This milling is necessarily carried out by the dry route and not by the wet route, as is generally the case for the processes of the glucose industries.

After having dry milled the corn kernels and/or cobs 20 in the mill 100, the milled product 131 is recovered and mixed with a stream of water in the mixer 102, in which a liquefaction stage (hydrolysis of the starch to give maltodextrins and oligosaccharides) is carried out to form a slurry 103, followed by a saccharification stage 104 (conversion of the complex sugars into simple sugars, such as glucose).

After the saccharification stage 104, the dextrose flow is separated into two parts, one liquid 108, which constitutes the main flow and contains the dextrose flow, with a dextrose content DE (Dextrose=Glucose Equivalent) of the order of 80%, and a second solid part 21 consisting of the secondary flow which comprises the components which are difficult to ferment.

This secondary flow 21 comprises in particular the fibrous elements, the germs, and proteins.

According to one embodiment of the process of the disclosure, the main flow 108 is subsequently treated so as to remove the oil, via the flow 25, which results from the milling of the corn kernels; after this first purification, the main flow 110 is subjected to a filtration stage 115 and the oligosaccharides are separated therefrom via the flow 29, so as to have a relatively pure dextrose flow 116 (DX (glucose percentage) >95%, indeed even >99%), so as to be subjected to the fermentation 118 in the presence of a microorganism 26 of a bacterium, yeast, or mold type, to produce lactic acid 28.

Still according to one embodiment of the process of the disclosure, the secondary flow 21 is recovered, and the oligosaccharides 29 recovered from the main flow 108 are added thereto so as to send it to a stage of hydrolysis in a reactor 113 in the presence of a strong acid. The resulting flow 114 is directed to a second fermenter 120 to convert this second dextrose flow into alcohol, to produce bioethanol or butanol, and/or into biogas.

BRIEF DESCRIPTION OF THE DRAWINGS

The process of the present disclosure is also described by way of the following figure: FIG. 1 is a schematic diagram (of an embodiment) of the process of the disclosure starting from the dry milling in the mill 100 of the corn cobs 20 so as to produce two dextrose flows, one configured to produce, as first fermentation product, lactic acid 28 and the other configured to produce a second fermentation product 101, such as an alcohol or biogas.

DETAILED DESCRIPTION

According to FIG. 1, a description is given of a system for dry grinding, in a mill 100, the corn cobs 20, so as to produce, in the end, two dextrose (flows or) streams, as will be described below.

After passing through the dry milling in a mill 100, the corn flour thus obtained and also the remainder 131 of the milled product comprising the fibers, the germs, and the components which are difficult to ferment are subsequently introduced into the mixer 102, where they are mixed with a stream of fresh water and a stream of recycling water from a subsequent stage of the process. It is also possible to add an enzyme 27, such as α-amylase, to this mixer 102. It is possible, if necessary, to heat the slurry obtained 103 to a temperature of between 60 and 100° C. for a period of 30 to 120 minutes. This results in the slurry 103.

This slurry 103, which contains the corn kernels, the germs, the fibers, the proteins, and also the oil which results from the milling of the corn kernels, is then sent to the saccharification stage 104. The dry solids content of this slurry 103 represents approximately 25% to 40% by weight.

The saccharification stage 104 produces a crude dextrose flow 105.

According to one embodiment of the process of the disclosure, the saccharification reaction 104 is carried out in two stages.

During the first stage, the pH is first adjusted to between 3.5 and 7.0 while maintaining the temperature between ambient temperature and 100° C. for a period of 1 to 6 hours, so as to convert the insoluble starch into dextrose. It is also possible to add a catalyst to carry out the reaction, such as α-amylase, in a proportion of 0.01% to 0.1% by weight.

During the second stage, the pH is readjusted to a value of between 4.0 and 5.0 while heating at a temperature ranging from ambient temperature to 180° C. for a period of 2 to 5 hours, to complete the conversion of the insoluble starch into dextrose. In this stage also, it is possible to add a catalyst, such as glucoamylase or α-amylase, in a proportion of 0.01% to 0.2% by weight.

The dextrose flow 105 thus recovered has a dextrose content of approximately 90 DE.

After the saccharification stage 104, a first separation is carried out in the crude dextrose flow 105 by passing it over a filter 106 which will separate the liquid part 108 from the solid part 21. The solid part comprises the fibers, the germs, and the grits, and also the components which are difficult to ferment.

This solid part 21 is then sent, via the pipe 121, to a reactor 113 to be treated so as to be converted into a fermentable dextrose (flow or) stream 114.

Moreover, the liquid part 108 resulting from the separator is sent to another separator 109 to remove the oil originating from the milling of the corn kernels. The separation of this oil is carried out by a method well known to a person skilled in the art.

The oil extracted is recovered via the pipe 117 to be purified and used for other purposes.

The dextrose flow 110, which is virtually devoid of oil, is optionally filtered 115a further time to remove any solid particles, before being sent to a reactor to remove the oligosaccharides 29 and to obtain a dextrose flow 116 which is as pure as possible, before being subjected to the fermentation 118.

According to preferred embodiment of the process of the disclosure, to facilitate fermentation, a high productivity, and a more easily manageable impurity profile in the production of lactic acid 28, it is preferable to increase the purity of the dextrose flow 116 to a DX content of 99%. In this context, the dextrose flow 110 will be subjected to a stage of selective separation of the sugars 111, it being possible for this separation to include a chromatography (stage) coupled with a microfiltration and/or demineralization (no particle being able to enter the chromatography). A stage of concentration prior to the chromatography can also be carried out so as to be able to carry out the chromatography under the optimum conditions.

The oligosaccharides 29 thus recovered are sent, via a pipe 112, to a reactor 113, where they are mixed with the flow 21 from the pipe 121, so as to be converted therein into a fermentable dextrose flow 114.

After this last separation 111, the resulting dextrose flow 116 is sent to the fermenter to be subjected therein to a fermentation stage 118. A microorganism 26, which produces lactic acid 28, such as *Lactobacillus, Bacillus, Sporolactobacillus*, or others, under operating conditions well known for carrying out this operation, is added to the fermenter.

Simultaneously, the solid fraction 21 recovered from the successive separation stages (by successively using two separators 106 and 107) (via the pipe 121) and the oligosaccharides 29, via the pipe 112, are sent to a mixing reactor 113. The mixture is subjected to a hydrolysis to render them fermentable. This hydrolysis is carried out with a large amount of water, generally representing from 50% to 80% of the mixture, at a temperature of between 140 and 180° C., generally in the presence of a strong acid and for a period of time of 15 to 120 minutes. Subsequent to the hydrolysis reaction, a fermentable dextrose stream 114 is obtained, which is sent, via a pipe, to the fermenter 120, to which a microorganism 26 is added thereto which will convert the second dextrose (flow or) stream into alcohol, such as butanol, or ethanol, to be used as bioethanol, and/or into biogas.

For the production of alcohol, the possible microorganisms will be yeasts, such as *Saccharomyces, Schizosaccharomyces, Zymomonas mobilis*, or others, or bacteria, such as *Clostridia, Escherichia coli, Pseudomonas putida*, or others.

The system, used in the present disclosure, to continuously produce, simultaneously, two dextrose streams starting from a dry milling of cereals, comprises:
- a grain mill 100 equipped to carry out a dry milling,
- a mixing vessel 102 (or mixer) for preparing a slurry 103 resulting from the mixing of the milled product 131 with a stream of water,
- a saccharification reactor (a reactor for carrying out a saccharification stage) 104,
- a separating filter 106 for giving two dextrose flows, one 108 containing the liquid matter, the other 21 containing the solid matter and resulting from two successive separation stages (by successively using two separators 106 and 107),
- a separator 109 for removing the oil from the dextrose flow 108, and recovering a purified dextrose flow 110,
- a system for separation by chromatography for removing the oligosaccharides 29 from the purified dextrose flow 110 (the purified dextrose flow 110 resulting from the separation carried out in the separator 109; or, in other words, the purified dextrose flow 110 recovered from the stage for separation of the oils),
- a fermenter (for carrying out a fermentation stage 118) for producing lactic acid 28, and
- a fermenter 120 for producing an alcohol or a biogas.

The process of the present disclosure is also described by way of an example below, which does not in any way constitute a limitation thereof.

Example

Corn cobs 20 are dry milled in an appropriate mill 100 at ambient temperature and the components 131 which result from the milling are sent to a mixer 102 to carry out a liquefaction stage therein.

A mixture of recycling water from the process and also a contribution of fresh water are introduced into this stirred vessel. Although it is possible to add as much water as desired, the amount necessary to render the mixture pumpable is added.

This mixture is heated at a temperature of 65° C. for 75 min in the presence of α-amylase as enzyme-catalyst in a proportion of 0.01% by weight, with respect to the mixture.

The resulting slurry 103 is then sent to the first saccharification stage 104.

This slurry contains 33% of dry solids.

The pH of the mixture is adjusted to 4.5 by addition of an acid, in this example sulfuric acid, and the mixture was heated at 63° C. for 3 hours, also in the presence of a catalyst, in this example α-amylase used in a proportion of 0.04% by weight.

The mixture is recovered and is subjected to the second saccharification stage 104, during which the pH is readjusted to between 4.1 and 4.3 while maintaining the temperature of the mixture at 61° C. for 5 hours.

A liquid flow 105 of crude dextrose having a dextrose content of 90 DE was thus obtained.

This crude dextrose flow 105 is passed over a filter 106 to separate the solid part 21 from the liquid part 108. The solid part 21 is recovered so as to be sent, via a pipe 121, to a reactor 113.

The liquid dextrose flow 108 is then subjected to a fresh separation in a separator 109 so as to remove the supernatant oil which results from the milling of the corn kernels.

The dextrose flow 110 resulting from this separation, this flow 110 being virtually devoid of oil, is subjected to a selective separation of the sugars 111 by chromatography, which makes it possible to recover the remaining oligosaccharides 29 and to send them, via the pipe 112, to the reactor 113 with the insoluble and non-fermentable components 21.

The purified (99 DX) dextrose flow 116 resulting from this last separation 111 is sent to the fermenter 118 to carry out a fermentation stage therein so as to be converted into lactic acid 28 therein after addition of an appropriate microorganism 26, in this instance a *Lactobacillus*.

Moreover, the mixture which arrives at the reactor 113 is subjected to a hydrolysis in the presence of a strong acid, in this instance hydrochloric acid, in a proportion of 4% by weight of acid, with respect to the weight of solids present.

This mixture is subsequently heated at 150° C. for 2 hours.

At the end of the operation, a dextrose flow is obtained and is directed to the fermenter 120 to produce ethanol in the presence of an appropriate yeast, in this instance *Saccharomyces cervisiae*.

LIST OF REFERENCE SYMBOLS 20 cereals (such as, for example, corn kernels and/or cobs)
21 solid (dextrose) flow
25 oil(s)
26 microorganism
27 enzyme
28 lactic acid
29 oligosaccharides (DPn)
100 mill
101 second fermentation product
102 mixer (or mixing vessel)
103 slurry
104 saccharification (stage)

105 crude (dextrose) flow or current
106 separator (such as, e.g., filter)
107 separator (such as, e.g., filter)
108 liquid (dextrose) flow or current
109 separator
110 purified dextrose flow
111 (stage of) selective separation of the sugars
112 pipe
113 hydrolysis reactor
114 fermentable dextrose flow
115 filtration (stage)
116 purified dextrose flow
117 pipe
118 fermentation (stage)
120 fermenter
121 pipe
130 oil refining (stage)
131 milled product (or result of the dry milling)

The invention claimed is:

1. A continuous process for the simultaneous production of lactic acid and of a second fermentation product starting from cereals, the process comprising:
    dry milling cereals using a mill to form a milled product;
    recovering the milled product and mixing it in a mixer with a stream of water to create a slurry;
    subjecting the slurry to a saccharification in a reactor and producing a crude dextrose stream;
    separating, in a separator, the crude dextrose stream into a first flow comprising a liquid flow and a second flow comprising solid part;
    removing an oil resulting from the milling and occurring in the liquid flow for subsequent treatment, and recovering a purified dextrose flow;
    producing a fermentation product in the form of a lactic acid by subjecting the purified dextrose flow to a selective separation of sugars to recover a purified flow and a flow rich in oligosaccharides, before subjecting the purified flow to a fermentation in the presence of a microorganism appropriate for producing the lactic acid;
    recovering the solid dextrose flow via a first pipe containing products which are difficult to ferment, and recovering the flow rich in oligosaccharides via a second pipe, to hydrolyze contents of the first and second pipes in a reactor under hydrolysis conditions and to convert the contents into a fermentable dextrose flow; and
    subjecting the fermentable dextrose flow to a fermentation in a fermenter to produce a second fermentation product.

2. The process as claimed in claim 1, wherein the selective separation of the sugars from the purified dextrose flow is carried out by chromatography.

3. The process as claimed in claim 1, wherein the hydrolysis in the reactor is carried out in the presence of a strong acid at a temperature of between 140 and 180° C., for a period of 30 minutes to 2 hours.

4. The process as claimed in claim 1, wherein the second fermentation product is selected from the group consisting of an alcohol and a biogas.

5. The process as claimed in claim 4, wherein the alcohol is ethanol or butanol.

6. The process as claimed in claim 1, wherein the cereals are selected from the group consisting of corn kernels and cobs.

7. The process as claimed in claim 1, wherein the microorganism is selected from the group consisting of *Saccharomyces, Schizosaccharomyces, Zymomonas mobilis*, Clostridia, *Escherichia coli* or Pseudomonasputida.

8. A system for continuously producing, simultaneously, two dextrose streams starting from a dry milling of cereals, the system comprising:
    a grain mill equipped for a dry milling;
    a mixing vessel configured to prepare a slurry resulting from mixing of a milled product from the grain mill with a stream of water;
    a saccharification reactor;
    a first separator configured to produce two dextrose flows from the crude dextrose stream, a first flow containing a liquid matter, and a second flow containing a solid matter;
    a second separator configured to remove oil from the first flow containing the liquid matter, and to recover a purified dextrose flow;
    a system for separation by chromatography to remove oligosaccharides from the purified dextrose flow;
    a first fermenter configured to produce lactic acid; and
    a second fermenter configured to produce an alcohol or a biogas.

* * * * *